United States Patent [19]

Bulteau et al.

[11] 4,029,673
[45] June 14, 1977

[54] N-(1-BENZYL PYRROLIDINYL 2-ALKYL) SUBSTITUTED BENZAMIDES AND DERIVATIVES THEREOF

[75] Inventors: Gerard Bulteau, Paris; Jacques Acher, Itteville; Jean-Claude Monier, Lardy, all of France

[73] Assignee: Societe d'Etudes Scientifiques et Industrielles de l'Ile-de-France, Paris, France

[22] Filed: Mar. 5, 1975

[21] Appl. No.: 555,376

[30] Foreign Application Priority Data

Mar. 5, 1974 France .............................. 74.7535
Feb. 7, 1975 France .............................. 75.3799

[52] U.S. Cl. ...................... 260/326.47; 260/326 A; 424/274
[51] Int. Cl.² ............. C07D 207/08; A61K 31/405
[58] Field of Search ............... 260/326.47; 424/274

[56] References Cited

UNITED STATES PATENTS

| 3,342,826 | 9/1967 | Miller et al. | 260/293.77 |
| 3,708,497 | 1/1973 | Kamiya et al | 260/326.8 |
| 3,862,139 | 1/1975 | Podesva et al. | 260/326.47 |
| 3,891,671 | 6/1975 | Thominet | 260/326.47 |
| 3,923,829 | 12/1975 | Denzler | 260/326.47 |

*Primary Examiner*—Donald G. Daus
*Assistant Examiner*—Diana G. Rivers
*Attorney, Agent, or Firm*—Frank M. Nolan

[57] ABSTRACT

The benzamides of this invention and their pharmaceutically acceptable salts are particularly effective in the treatment of emesis and ulcers in mammals. Their low level of toxicity is compatible with use in human therapy, without undesirable side effects.

3 Claims, No Drawings

N-(1-BENZYL PYRROLIDINYL 2-ALKYL) SUBSTITUTED BENZAMIDES AND DERIVATIVES THEREOF

This invention relates to N-(1-benzyl pyrrolidinyl 2-alkyl) substituted benzamides, their pharmaceutically acceptable acid addition salts, their quaternary ammonium salts, and processes for the production of such compounds.

The benzamides of this invention have the following formula:

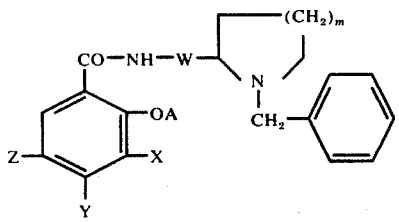

in which:
A is hydrogen, alkyl having 1 to 5 carbon atoms, or alkenyl having 2 to 5 carbon atoms;
X is hydrogen, alkoxy having 1 to 5 carbon atoms, alkyl having 1 to 5 carbon atoms, alkenyloxy having 2 to 5 carbon atoms or alkenyl having 2 to 5 carbon atoms;
Y is hydrogen, halogen, alkyl having 1 to 5 carbon atoms, alkoxy having 1 to 5 carbon atoms, amino, or substituted amino such as alkylamino, acylamino, benzylamino or alkoxycarbonylamino, the substituent of the substituted amino having less than 11 carbon atoms;
Z is hydrogen, halogen, alkoxy having 1 to 5 carbon atoms, alkylsulfonyl having 1 to 5 carbon atoms, or an $SO_2NR_1R_2$ group in which $R_1$ and $R_2$ may be identical or different and are hydrogen or alkyl of 1 to 5 carbon atoms, or together with the nitrogen atom to which they are attached, form a heterocyclic group with or without oxygen, sulfur or an additional nitrogen atom;
W is alkylene which may be a straight or branched chain having from 1 to 4 carbon atoms; and
m is 1, 2 or 3.

Since the benzamides of Formula (I) or the derivatives thereof have an asymmetric carbon atom, such compounds may be dextrorotary, levorotary or racemic isomers. If desired, the compounds of this invention may be utilized in a form which consists of only the dextro or levo isomer which is substantially free of the corresponding other stereo-isomer.

The benzamides of this invention are produced by reacting a compound having the formula:

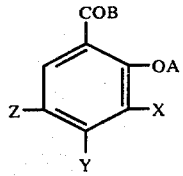

in which:
B is an amination effecting reactive radical or element, such as halogen, hydroxy or alkoxy having 1 to 5 carbon atoms with a dextrorotary, levorotary or racemic amine or its reactive derivatives, the amine having the formula:

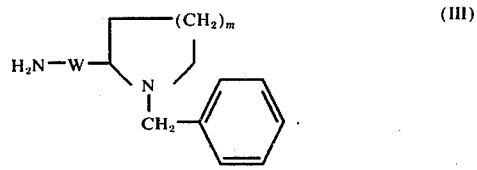

Throughout the description of this invention, the definitions A, B, X, Y, Z, W and m are the same.

In the starting compound (II) the amination effecting reactive radical or element B is capable of reacting with the amino group of the amine of Formula (III) or with derivatives of that amine. If the amination effecting reactive radical or element is hydroxy, the resulting benzoic acid conforming to Formula (II) reacts with the amino group of the amine of Formula (III) to produce the compounds of Formula (I). If B is alkoxy, esters of benzoic acids falling within the scope of Formula (II) constitute the starting material. Examples of such esters are alkyl esters such as methyl, ethyl, propyl, butyl, isobutyl or pentyl esters; reactive acid esters such as cyanomethyl or methoxymethyl esters; n-hydroxyimide esters or substituted or unsubstituted aromatic esters. Other examples of starting materials are derivatives of benzoic acids falling within the scope of Formula (II) such as acid hydrazides; acid azides; symmetrical anhydrides; mixed anhydrides, e.g. formed with lower alkyl haloformates; azolides such as triazolides, tetrazolides or imidazolides; or acid isocyanates.

According to the processes of the invention, the following compounds may be used as reactive derivatives of the amine (III): the products of reaction of the amine with phosphorus chlorides, phosphorus oxychloride, dialkyl, diaryl or orthophenylenechlorophosphites, alkyl or aryl dichlorophosphites, or the isothiocyanate of the amine. The reactive derivatives listed above can react with the acid in situ or after having first been isolated.

It is also possible to carry out the reaction of the free acid and the free amine in the presence of a condensing agent such as silicon tetrachloride, phosphoric anhydride or a carbodiimide such as dicyclohexyl carbodiimide.

The amination reaction of the invention may be carried out in the presence or in the absence of solvent. The systems used as a solvent, which are inert with respect to the reaction, may be alcohols, polyols, benzene, toluene, dioxan, chloroform, diethyleneglycol or dimethylether. It is also possible to use as a solvent an excess of the amine used as the starting material. It may be preferable to heat the reaction mixture during amination, for example, to the boiling point of the solvents listed above.

To produce the acid addition salts of the benzamides, the benzamides of Formula (I) are reacted with pharmaceutically acceptable mineral or organic acids such as hydrochloric acid, hydrobromic acid, sulfuric acid, phosphoric acid, acetic acid, tartaric acid, citric acid or methane sulfonic acid. To produce the quaternary ammonium salts, the benzamides of Formula (I) are reacted with alkyl sulfates or halides.

Examples of the aminosubstituted groups represented by Y are alkylaminos such as mono or dialkylaminos in which each alkyl group has 1 to 5 carbon atoms, and acylaminos such as acetamido, formamido, propionamido, butyramido, benzamido or phthalimido.

A more comprehensive understanding of this invention is obtained by reference to the following examples:

EXAMPLE I

N-(1'-BENZYL PYRROLIDINYL 2'-METHYL)-2-METHOXY 5-ETHYLSULFONYLBENZAMIDEHYDROCHLORIDE 2160 mo of methylethylketone and 400 g of N-benzyl 2-amino-methyl pyrrolidine were introduced into a 6 liter reaction vessel provided with a mechanical stirrer and a thermometer. 540 g of 2-methoxy 5-ethylsulfonyl benzoyl chloride were then added, the temperature being maintained at from 15° to 20° C. Stirring of the mixture was maintained for 3 hours at ambient temperature. The crystals formed were drained, washed with a little ice-cold methylethylketone and dried at 50° C. 850 g of crystals was obtained. The crystals were dissolved in 4250 ml of 95% isopropanol. After filtration, the solution was cooled. The crystals formed were drained, washed and dried. 700 g (yield: 75.5%) of N-(1'-benzyl pyrrolidinyl 2'methyl) 2-methoxy 5-ethylsulfonylbenzamidehydrochloride, having a melting point of 170° were produced.

EXAMPLE II

N-(1'-BENZYL PYRROLIDINYL 2'-METHYL) 2-METHOXY 5-METHYLSULFONYLBENZAMIDEHYDROCHLORIDE

Introduced into a 10 liter reaction vessel provided with a mechanical stirrer and a thermometer were 3 liters of methylethylketone and 431 g of N-benzyl 2-aminomethyl pyrrolidine. Then, with the temperature being maintained at from 15° to 20° C, 555 g of 2-methoxy 5-methylsulfonylbenzoylchloride were added.

Stirring of the reaction mixture was continued for 2 hours at ambient temperature. The solid formed was drained and treated with ice-cold methylethylketone, then dried at 50° C. 935 g of product was obtained.

Purification of this product was carried out by conversion of the hydrochloride formed into a base by treatment with ammonia, then aslification of this base by means of an acid. Salification was carried out with hydrochloric ethanol after the base had been dissolved in 3 liters of ethanol.

The hydrochloride formed was drained, washed with ice-cold ethanol and dried at 50° C. 825 g (yield: 84.3%) of N-(1'-benzyl-pyrrolidinyl 2'-methyl) 2-methoxy 5-methylsulfonylbenzamidehydrochloride having a melting point of 153°–156° C were produced.

EXAMPLE III

N-(1'-BENZYL PYRROLIDINYL 2'-METHYL) 2-METHOXY 4-AMINO 5-SULFAMOYL BENZAMIDEPHOSPHATE 500 g of methyl 2-methoxy 4-amino 5-sulfamoylbenzoate, 510 ml of water and 547 g of 1-benzyl 2-aminomethylpyrrolidine were introduced into a 4 liter balloon flask provided with a mechanical stirrer, a thermometer and a reflux condenser. After the addition operation, the mixture was heated at 90° to 95° C for 20 hours. The solid which was deposited after cooling was extracted three times with 700 ml of methylenechloride.

The extraction solvents were combined, washed with water, dried over magnesium sulfate, and evaporated under reduced pressure.

The product obtained (450 g) was dissolved at boiling temperature in 1350 ml of water and 250 ml of 85% phosphoric acid was added (pH value 1). The crystals formed by cooling were redissolved in 1350 ml of water at boiling temperature; then 40 g of activated carbon were added. After filtration in the hot condition and cooling of the solution obtained, the crystals formed were drained, washed with water and dried in a drying oven at 50° C. 380 g of N-(1'-benzylpyrrolidinyl 2'-methyl) 2-methoxy 4-amino 5-sulfamoylbenzamidephosphate having a melting point of 184°–186° C were produced.

EXAMPLE IV

N-(1'-BENZYLPYRROLIDINYL 2'-METHYL) 2-METHOXY 4-AMINO 5-CHLOROBENZAMIDINE 515 g of methyl 2-methoxy 4-acetamino 5-chlorobenzoate, 1100 ml of ethyleneglycol and, with stirring, 1140 g of N-benzyl 2-aminomethylpyrrolidine were introduced into a 6 liter balloon flask provided with a mechanical stirrer, a reflux condenser, a thermometer and a gas input tube. The mixture was heated at 120° C for 2 hours under an argon atmosphere, and after cooling to 100° C, 500 ml of an aqueous 2.5N sodium hydroxide solution which was first heated to from 95° to 100° C were added. The mixture was heated at the reflux temperature for 30 minutes. After the addition of a liter of water, the mixture was cooled to from 0° to 5° C. The organic oil which was separated off was decanted and dissolved in the 800 ml of methylenechloride which was used to extract the aqueous phase. After drying by means of magnesium sulfate, the solvent was evaporated under vacuum. The residue obtained was recrystallized from acetone.

The crystals obtained were drained and dried in a drying oven at 50° C. 350 g (yield: 47%) of N-(1'-benzylpyrrolidinyl 2'-methyl) 2-methoxy 4-amino 5-chlorobenzamide having a melting point of 142°–144° C were produced.

EXAMPLE V

N-(1'-BENZYLPYRROLIDINYL 2'-METHYL) 2-METHOXY 5-ETHYLSULFONYLBENZAMIDEHYDROCHLORIDE 713 g of 2-methoxy 5-ethylsulfonylbenzoic acid, 200 ml of tetrahydrofuran and 7.3 g of carbonyldiimidazole were introduced into a balloon flask provided with a stirrer and a condenser. After stirring of the mixture at ambient temperature for 30 minutes, 9.2 g of N-benzyl 2-aminomethylpyrrolidine were added. Stirring of the mixture was continued at ambient temperature, and then the solvent was evaporated under vacuum.

The residue was dissolved in hydrochloric acid. The filtered solution was treated with sodium hydroxide until the pH value was 12 to 13. The mixture was extracted with chloroform, the organic phase was dried and filtered and the solvent was evaporated under vacuum.

The benzamide produced was then converted into its hydrochloride by dissolution in ethanol and treatment with hydrochloric ethanol.

After the usual treatment (filtration, washing, drying in a drying oven), 8.5 g (yield: 63%) of N-(1'-benzylpyrrolidinyl 2'-methyl) 2-methoxy 5-ethylsulfonylbenzamidehydrochloride having a melting point of 170° C were obtained.

EXAMPLE VI

N-(1'-BENZYLPYRROLIDINYL 2'-METHYL) 2-METHOXY 4-AMINO 5-METHYLSULFAMOYLBENZAMIDE 220 g of 2-methoxy 4-amino 5-methylsulfamoylbenzoic acid, 217 ml of water and 85.5 g of triethylamine were introduced into a 3 liter balloon flask provided with a stirrer, a thermometer and a dropping funnel. The mixture was heated to about 50° C, until dissolution occurred. After 520 ml of acetone had been added to the mixture, the solution obtained was cooled to 0° C, and 92 g of ethylchloroformate were added dropwise at a temperature of from 0° to 5° C. Stirring of the mixture was continued at from 0° to 5° C for 1 hour, 30 minutes. Then 92 g of 1-benzyl 2-aminomethylpyrrolidine were added.

After the temperature had risen to ambient temperature, stirring of the mixture was maintained for 2 hours.

The acetone was then distilled, and the residue was redissolved in 2 liters of water. The mixture was rendered alkaline by the addition of 15 ml of 20% ammonia, and the base precipitated. The product was purified by formation of phosphate by the addition of 85% phosphoric acid. Then the base was re-precipitated by 20% ammonia. 228 g (yield: 62%) of N-(1'-benzylpyrrolidinyl 2'-methyl) 2-methoxy 5-methylsulfamoylbenzamide having a melting point of 88° –92° C were produced.

EXAMPLE VII

N-(1'-BENZYLPYRROLIDINYL 2'-METHYL) 2,3DIMETHOXY 5-SULFAMOYLBENZAMIDEHYDROCHLORIDE 1 liter of acetone and 200 g of N-benzyl 2-aminomethylpyrrolidine were introduced into a 4 liter balloon flask provided with a mechanical stirrer and a thermometer. The mixture was cooled to 0° C, and 280 g of 2,3-dimethoxy 5-sulfamoylbenzoylchloride were added, the temperature of the reaction medium being maintained at less than 10° C. Stirring of the mixture was continued for 4 hours. The precipitate formed was drained, washed over a filter, and dried at 50° C. Purification of the resulting product was effected by dissolution at boiling temperature in 600 ml of dimethylformamide. After filtration of the solution and cooling, the crystals obtained were drained, washed and then dried at 60° C. 190 g (yield: 38.5%) of N-(1'-benzylpyrrolidinyl 2'-methyl) 2,3-dimethoxy 5-sulfamoylbenzamide having a melting point of 208°–209° were produced.

EXAMPLE VIII

N-(1'-BENZYLPYRROLIDINYL 2'-METHYL) 2,3-DIMETHOXY 5-METHYLSULFAMOYLBENZAMIDE

Introduced into a 2 liter balloon flask were 500 g of ethyleneglycol in which were dissolved 124 g of methyl 2,3-dimethoxy 5-methylsulfamoylbenzoate at 50° C. 98 g of 1-benzyl 2-aminomethylpyrrolidine were added and the solution obtained was maintained at a temperature of 50° C until a test sample was entirely soluble in dilute acids. After dilution of the reaction mixture by 2 liters of water, followed by acidification with 70 ml of concentrated hydrochloric acid, the solution was treated with activated carbon and filtered. The base was precipitated with 20% ammonia.

The substance formed by the addition of a small amount of ether was then drained, washed with water and dried. By recrystallization from absolute ethanol, 127 g (yield: 84.5%) of N-(1'-benzylpyrrolidinyl 2'-methyl) 2,3-dimethoxy 5-methylsulfamoylbenzamide having a melting point of 121°–122° were produced.

EXAMPLE IX

N-(1'-BENZYLPYRROLIDINYL 2'-METHYL) 2-METHOXY 5-METHYLSULFAMOYLBENZAMIDE 238 g of ethyl 2-methoxy 5-methylsulfamoylbenzoate, 78.5 g of water and 198 g of 1-benzyl 2-aminomethylpyrrolidine were introduced into a 1 liter balloon flask provided with a condenser. The suspension obtained was heated at about 90° C until a test sample was entirely soluble in dilute acids. The mixture was then treated with 1550 ml of water, and acidified by means of concentrated hydrochloric acid. The resulting solution was treated with activated carbon and filtered, and then rendered alkaline by means of 20% ammonia. The solid substance formed by the addition of a small amount of either was drained, washed with water and dried at 45° C.

Recrystallization of the base from boiling absolute alcohol gave 211 g (yield: 58.5%) of N-(1'-benzylpyrrolidinyl 2'-methyl) 2-methoxy 5-methylsulfamoylbenzamide having a melting point of 117°–118.5° C.

EXAMPLE X

N-(1'-BENZYLPYRROLIDINYL 2'-METHYL) 2-METHOXY 4-AMINO 5-CHLOROBENZAMIDE

A solution of 1.4 g of phosphorus trichloride in 8 ml of pyridine was added dropwise, with stirring and with the temperature being maintained at from 0° to 5° C, to a solution of 3.5 g of 1-benzyl 2-aminomethylpyrrolidine in pyridine. Stirring was continued at from 0° to 5° C, then at ambient temperature.

After the addition of 2 g of 2-methoxy 4-amino 5-chlorobenzoic acid to the prepared solution, the mixture was heated with stirring for several hours.

After cooling of the mixture and removal of the solvent, the residue was dissolved in chloroform. The resulting solution was treated with aqueous sodium carbonate and dried by means of anhydrous magnesium sulfate.

The resulting solid, after concentration under reduced pressure, was recrystallized from acetone. 2.2 g (yield: 59.3%) of N-(1'-benzyl 2'-pyrrolidinylmethyl) 2-methoxy 4-amino 5-chlorobenzamide having a melting point of 142° –144° C were obtained.

EXAMPLE XI

N-(1'-BENZYL 2'-PYRROLIDYMETHYL) 2-METHOXY 5-SULFAMOYLBENZAMIDEHYDROCHLORIDE 571 g of ethyl 2-methoxy 5-sulfamoylbenzoate and 1320 ml of glycol were introduced into a 4 liter balloon flask. The temperature of the mixture was brought to 70° C. Then 420 g of N-benzyl 2-aminomethylpyrrolidine were added. The mixture was maintained at 120° C for 4 hours. After cooling, the substance obtained was suspended in water; the precipitate was filtered, and treated with a solution of 300 ml of 36% hydrochloric acid in 5 liters of water, stirring of the mixture being maintained for 2 hours.

The hydrochloride formed was drained, washed with water, and dried in a drying oven at 50° C. 900 g (yield: 93%) of N-(1'-benzyl 2'-pyrrolidylmethyl) 2-methoxy 5-sulfamoylbenzamidehydrochloride having a melting point of 232°–235° C were obtained.

The benzamides, or their salts, of this invention are particularly effective in the treatment of emesis and ulcers in mammals. Their low level of toxicity is compatible with use in human therapy, without undesirable side effects.

What is claimed is:

1. A compound selected from the class consisting of substituted benzamides and their pharmaceutically acceptable salts, said substituted benzamides having the formula:

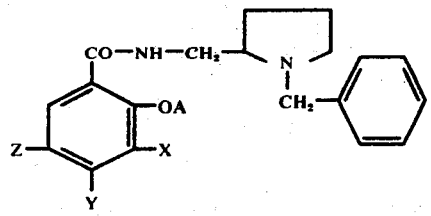

in which:
A is alkyl having 1 to 5 carbon atoms;
X is hydrogen or alkoxy having 1 to 5 carbon atoms;
Y is hydrogen or amino;
Z is hydrogen, halogen, sulfamoyl, alkylsulfamoyl or alkylsylfonyl having 1 to 5 carbon atoms, at least one of X, Y and Z being other than hydrogen, being N-(1'-benzylpyrrolidinyl 2'-methyl) 2-methoxy 4-amino 5-methylsulfamoylbenzamide or N-(1'-benzylpyrrolidinyl 2'-methyl) 2,3-dimethoxy 5-methylsulfamoylbenzamine.

2. A compound of claim 1 which is N-(1'-benzylpyrrolidinyl 2'-methyl) 2-methoxy 4-amino 5-methylsulfamoylbenzamide.

3. A compound of claim 1 which is N-(1'-benzylpyrrolidinyl 2'-methyl) 2,3-dimethoxy 5-methylsulfamoylbenzamide.

* * * * *

UNITED STATES PATENT OFFICE
CERTIFICATE OF CORRECTION

Patent No. 4,029,673   Dated June 14, 1977

Inventor(s) Gerard Bulteau et al

It is certified that error appears in the above-identified patent and that said Letters Patent are hereby corrected as shown below:

Claim 1 should read as follows:

1. A compound selected from the class consisting of substituted benzamides and their pharmaceutically acceptable salts, said substituted benzamides being N-(1'-benzylpyrrolidinyl 2'-methyl) 2-methoxy 4-amino 5-methylsulfamoylbenzamide or N-(1'-benzylpyrrolidinyl 2'-methyl) 2,3-dimethoxy 5-methylsulfamoyl-benzamide.

Signed and Sealed this

Third Day of January 1978

[SEAL]

Attest:

RUTH C. MASON
Attesting Officer

LUTRELLE F. PARKER
Acting Commissioner of Patents and Trademarks